United States Patent
Leytes et al.

[11] Patent Number: 6,025,985
[45] Date of Patent: Feb. 15, 2000

[54] MOVEABLE CONTROL UNIT FOR HIGH-THROUGHPUT ANALYZER

[75] Inventors: Lev J. Leytes, Palo Alto; William G. Burton, Pleasanton; Yong Paik, Danville; Glenn R. Edwards; Douglas N. Modlin, both of Palo Alto; Amer El-Hage, Menlo Park, all of Calif.

[73] Assignee: LJL BioSystems, Inc., Sunnyvale, Calif.

[21] Appl. No.: 09/118,341

[22] Filed: Jul. 16, 1998

Related U.S. Application Data

[63] Continuation of application No. 09/062,472, Apr. 17, 1998, and application No. PCT/US98/14575, Jul. 15, 1998

[60] Provisional application No. 60/052,876, Jul. 16, 1997, provisional application No. 60/059,639, Sep. 20, 1997, provisional application No. 60/063,811, Oct. 31, 1997, provisional application No. 60/072,499, Jan. 26, 1998, provisional application No. 60/072,780, Jan. 27, 1998, provisional application No. 60/075,414, Feb. 20, 1998, provisional application No. 60/075,806, Feb. 24, 1998, provisional application No. 60/082,253, Apr. 17, 1998, provisional application No. 60/084,167, May 4, 1998, provisional application No. 60/085,335, May 13, 1998, provisional application No. 60/085,500, May 14, 1998, and provisional application No. 60/089,848, Jun. 19, 1998.

[51] Int. Cl.[7] ........................................ G06F 1/16
[52] U.S. Cl. ............................ 361/679; 361/724
[58] Field of Search ......................... 361/681, 680, 361/686, 685, 679, 724–727, 608, 609, 675

[56] References Cited

U.S. PATENT DOCUMENTS

| | | |
|---|---|---|
| 2,719,214 | 9/1955 | Potter . |
| 3,013,467 | 12/1961 | Minsky . |
| 3,423,581 | 1/1969 | Baer . |
| 3,516,736 | 6/1970 | Weaver . |
| 3,849,654 | 11/1974 | Malvin . |
| 3,932,023 | 1/1976 | Humer . |
| 4,011,451 | 3/1977 | Nelson . |
| 4,067,653 | 1/1978 | Fletcher et al. . |
| 4,076,420 | 2/1978 | De Maeyer et al. . |
| 4,100,416 | 7/1978 | Hirschfeld . |
| 4,144,452 | 3/1979 | Harte . |
| 4,150,870 | 4/1979 | d'Auria . |
| 4,203,670 | 5/1980 | Bromberg . |
| 4,341,957 | 7/1982 | Wieder . |
| 4,451,149 | 5/1984 | Noeller . |
| 4,485,430 | 11/1984 | Achiaga Fustel . |
| 4,501,970 | 2/1985 | Nelson . |
| 4,567,847 | 2/1986 | Linner ................................. 422/131 |
| 4,626,684 | 12/1986 | Landa ................................. 250/328 |
| 4,685,801 | 8/1987 | Minekane . |
| 4,699,512 | 10/1987 | Koshi . |
| 4,704,255 | 11/1987 | Jolley . |
| 4,707,067 | 11/1987 | Haberland et al. . |
| 4,724,217 | 2/1988 | Miller . |
| 4,730,921 | 3/1988 | Klein et al. . |
| 4,738,825 | 4/1988 | Kelln et al. . |
| 4,741,619 | 5/1988 | Humphries . |
| 4,753,501 | 6/1988 | Battle . |
| 4,762,420 | 8/1988 | Bowley . |
| 4,772,453 | 9/1988 | Lisenbee . |
| 4,784,275 | 11/1988 | Fridge ................................. 209/558 |
| 4,810,096 | 3/1989 | Russell et al. . |

(List continued on next page.)

FOREIGN PATENT DOCUMENTS

| | | |
|---|---|---|
| 0 266 881 A2 | 5/1988 | European Pat. Off. . |
| 2 215 838 | 9/1989 | United Kingdom . |
| 2 228 081 | 8/1990 | United Kingdom . |

OTHER PUBLICATIONS

*Fundamentals of Light Microscopy*, Spencer, Cambridge University Press, 1982.

*Primary Examiner*—Leo P. Picard
*Assistant Examiner*—Lisa Lea-Edmonds
*Attorney, Agent, or Firm*—Kolisch, Hartwell, Dickinson, McCormack & Heuser

[57] ABSTRACT

A moveable control unit for a high-throughput analyzer that can be operatively mounted at a plurality of locations on the analyzer housing.

22 Claims, 2 Drawing Sheets

U.S. PATENT DOCUMENTS

| | | |
|---|---|---|
| 4,826,660 | 5/1989 | Smith et al. . |
| 4,855,930 | 8/1989 | Chao et al. . |
| 4,868,103 | 9/1989 | Stavrianopoulos et al. . |
| 4,873,633 | 10/1989 | Mezei et al. . |
| 4,877,965 | 10/1989 | Dandliker et al. . |
| 4,885,087 | 12/1989 | Kopf ................................. 210/321.72 |
| 4,892,409 | 1/1990 | Smith . |
| 4,923,819 | 5/1990 | Fernandez et al. . |
| 4,936,682 | 6/1990 | Hoyt . |
| 4,948,442 | 8/1990 | Manns . |
| 4,968,148 | 11/1990 | Chow et al. . |
| 4,979,821 | 12/1990 | Schutt et al. . |
| 5,009,488 | 4/1991 | Fay et al. . |
| 5,039,219 | 8/1991 | James et al. . |
| 5,047,215 | 9/1991 | Manns . |
| 5,058,045 | 10/1991 | Ma ................................................ 361/686 |
| 5,082,628 | 1/1992 | Andreotti et al. . |
| 5,084,246 | 1/1992 | Lyman et al. . |
| 5,091,652 | 2/1992 | Mathies et al. . |
| 5,095,517 | 3/1992 | Monguzzi et al. . |
| 5,096,807 | 3/1992 | Leaback . |
| 5,169,601 | 12/1992 | Ohta et al. . |
| 5,192,510 | 3/1993 | Zoha et al. . |
| 5,206,568 | 4/1993 | Bjornson et al. . |
| 5,208,161 | 5/1993 | Saunders et al. . |
| 5,208,651 | 5/1993 | Buican . |
| 5,225,164 | 7/1993 | Astle . |
| 5,257,202 | 10/1993 | Feddersen et al. . |
| 5,270,788 | 12/1993 | Cercek et al. . |
| 5,273,718 | 12/1993 | Sköld et al. . |
| 5,275,951 | 1/1994 | Chow et al. . |
| 5,315,015 | 5/1994 | Hui et al. . |
| 5,317,485 | 5/1994 | Merjanian . |
| 5,319,436 | 6/1994 | Manns et al. . |
| 5,323,008 | 6/1994 | Studholme et al. . |
| 5,340,716 | 8/1994 | Ullman et al. . |
| 5,340,747 | 8/1994 | Eden . |
| 5,355,215 | 10/1994 | Schroeder et al. . |
| 5,361,626 | 11/1994 | Colligan et al. ........................ 73/40.7 |
| 5,384,093 | 1/1995 | Ootani et al. . |
| 5,401,465 | 3/1995 | Smethers et al. . |
| 5,418,371 | 5/1995 | Aslund et al. . |
| 5,420,408 | 5/1995 | Weyrauch et al. . |
| 5,436,718 | 7/1995 | Fernandes et al. . |
| 5,445,935 | 8/1995 | Royer . |
| 5,449,921 | 9/1995 | Baba . |
| 5,457,527 | 10/1995 | Manns et al. . |
| 5,459,300 | 10/1995 | Kasman . |
| 5,480,804 | 1/1996 | Niwa et al. . |
| 5,485,530 | 1/1996 | Lakowicz et al. . |
| 5,487,872 | 1/1996 | Hafeman et al. . |
| 5,491,343 | 2/1996 | Brooker . |
| 5,512,492 | 4/1996 | Herron et al. . |
| 5,528,046 | 6/1996 | Ishikawa . |
| 5,537,343 | 7/1996 | Kikinis et al. .......................... 361/686 |
| 5,542,012 | 7/1996 | Fernandes et al. . |
| 5,557,398 | 9/1996 | Wechsler et al. . |
| 5,589,136 | 12/1996 | Northrup et al. . |
| 5,589,350 | 12/1996 | Bochner . |
| 5,589,351 | 12/1996 | Harootunian . |
| 5,592,289 | 1/1997 | Norris . |
| 5,593,867 | 1/1997 | Walker et al. . |
| 5,595,710 | 1/1997 | Van Dusen et al. . |
| 5,599,500 | 2/1997 | Jones . |
| 5,604,130 | 2/1997 | Warner et al. . |
| 5,620,894 | 4/1997 | Barger et al. . |
| 5,626,134 | 5/1997 | Zuckerman . |
| 5,631,734 | 5/1997 | Stern et al. . |
| 5,633,724 | 5/1997 | King et al. . |
| 5,635,402 | 6/1997 | Alfano et al. . |
| 5,641,633 | 6/1997 | Linn et al. . |
| 5,663,545 | 9/1997 | Marquiss . |
| 5,676,943 | 10/1997 | Baetge et al. . |
| 5,679,310 | 10/1997 | Manns . |
| 5,736,410 | 4/1998 | Zarling et al. . |
| 5,780,857 | 7/1998 | Harju et al. . |
| 5,825,617 | 10/1998 | Kochis et al. .......................... 361/686 |
| 5,842,582 | 12/1998 | DeStefano, Jr. . |

MOVEABLE CONTROL UNIT FOR HIGH-THROUGHPUT ANALYZER

CROSS-REFERENCES TO RELATED APPLICATIONS

This application is a continuation of the following patent applications, each of which is incorporated herein by reference: U.S. patent application Ser. No. 09/062,472, filed Apr. 17, 1998; and PCT Patent Application Ser. No. PCT/U.S. Pat. No. 98/14575, filed Jul. 15, 1998.

This application is based upon and claims benefit under 35 U.S.C. §119 of the following U.S. Provisional Patent Applications, each of which is incorporated herein by reference: Ser. No. 60/052,876, filed Jul. 16, 1997; Ser. No. 60/059,639, filed Sep. 20, 1997; Ser. No. 60/063,811, filed Oct. 31, 1997; Ser. No. 60/072,499, filed Jan. 26, 1998; Ser. No. 60/072,780, filed Jan. 27, 1998; Ser. No. 60/075,414, filed Feb. 20, 1998; Ser. No. 60/075,806, filed Feb. 24, 1998; Ser. No. 60/082,253, filed Apr. 17, 1998; Ser. No. 60/084,167, filed May 4, 1998; Ser. No. 60/085,335, filed May 13, 1998; Ser. No. 60/085,500, filed May 14, 1998; and Ser. No. 60,089,848, filed Jun. 19, 1998.

This application incorporates by reference the following U.S. patent applications Ser. No. 09/118,310, filed Jul. 16, 1998; and Ser. No. 09/118,141, filed Jul. 16, 1998.

FIELD OF THE INVENTION

The invention relates to control units. More particularly, the invention relates to moveable control units that permit operation of a high-throughput analyzer from a plurality of locations.

BACKGROUND OF THE INVENTION

High-throughput screening instruments (or analyzers) are critical tools in the pharmaceutical research industry and in the process of discovering and developing new drugs. High-throughput analyzers are used to assess the efficacy of candidate drug compounds. Dramatic increases in the number of these compounds and in the number of targets against which they may be directed has created a bottleneck in the development of new drugs and a need for instruments that can operate with a high degree of analytical flexibility and speed. Analytical flexibility and speed are necessary because high-throughput applications may involve repeating the same operations hundreds of thousands of times, greatly magnifying even the smallest shortcomings. Recently, robots and other devices have been used to speed up and automate many high-throughput screening procedures.

High-throughput analyzers typically are contained in a housing that has a sample input port on one side. For some high-throughput applications, it is most convenient and efficient to use the analyzer in a manual mode, in which an operator stands in front of or near the side of the instrument where the input port is located. In this case, it also is convenient to have a control unit located on the same side as the input port, so that the operator can interact with the control unit while overseeing the sample feeding process.

For other high-throughput applications, it is preferable to employ ancillary robotic mechanisms to feed samples in and out of the instrument automatically, through the input port. Yet, if the control unit is on the same side as the input port, it may be awkward or even impossible for the an operator to access the control unit without interfering with or encumbering these ancillary robotic mechanisms.

SUMMARY OF THE INVENTION

The present invention addresses these and other shortcomings by providing a device and method for controlling an analyzer from a plurality of locations.

In one embodiment, the invention provides a device comprising (1) a plurality of control interface docking locations disposed on a housing containing the analyzer, and (2) a control unit that can be mounted at any one of the docking locations, so that a user can control the analyzer by inputting information through the control unit. The control unit can be moved from one docking location to another to provide convenience in different modes of operation.

In another embodiment, the invention provides a device comprising (1) a first control interface docking location on or near an upper edge of a first side of a housing containing the analyzer, and (2) a control unit that can be operatively mounted at the first control interface docking location. A sample input port is included on the first side of the housing. The control unit can be operatively relocated at a second control interface docking location remote from the first side. The second control interface docking location may be located on or near a second side of the housing, or spaced apart from the housing.

Preferred embodiments further may include particular geometries, functionalities, and docking locations for the control unit, as well as additional control units.

In yet another embodiment, the invention provides a method of controlling an analyzer capable of being used in a manual mode or a robotic mode comprising (1) providing a control unit that can be mounted at a first or second docking location, wherein the docking locations are disposed on a housing containing the analyzer, (2) mounting the control unit in the first docking location when the analyzer is to be used in the manual mode, and (3) mounting the control unit in the second docking location when the analyzer is to be used in the robotic mode.

Preferred embodiments of the device and method further may include particular geometries, functionalities, and docking locations for the control unit, as well as additional control units.

The nature of the invention will be understood more readily after consideration of the drawings and the detailed description of the invention that follow.

DESCRIPTION OF THE INVENTION

Figure 1:
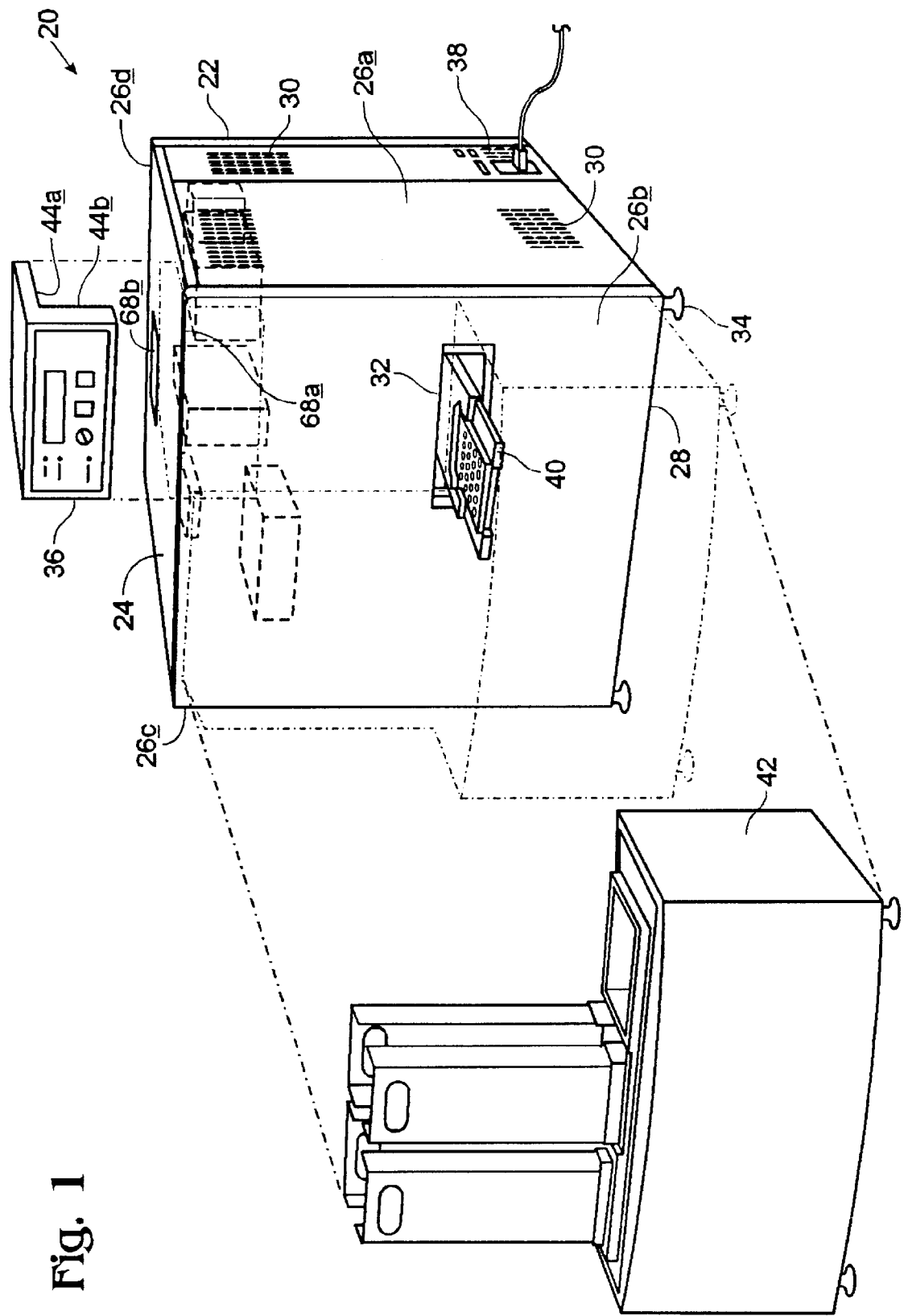
FIG. 1 is a perspective view of a high-throughput analyzer including a control unit and a sample feeding mechanism.

FIG. 1 shows a high-throughput luminescence analyzer 20 constructed in accordance with the invention. Components of the analyzer are maintained in a housing 22, both for organization and for protection. Housing 22 is substantially rectangular and includes light-tight exterior top 24, side 26a–d, and bottom walls 28 that reduce background in luminescence measurements. The walls may include vents 30 to facilitate air flow through the analyzer and a transporter port 32 for sample input/output. Housing 22 also may include feet 34 to support the analyzer and to permit air flow between the analyzer and any support structure on which the analyzer is placed.

Analyzer 20 is substantially automated. The analyzer is designed so that user interactions occur primarily through a control unit 36 and an electronic input/output panel 38, each of which supports a variety of input/output functions. The analyzer also is designed so that sample input/output occurs primarily through a transporter/stage 40 and an optional sample feeder 42.

Control unit 36 generally comprises any interface used for direct input/output functions. The control unit may be integrated into the analyzer, or it may be a separate unit that can be positioned away from the analyzer or affixed to the analyzer at one or more locations. The control unit also may include more than one unit, each dedicated to different input/output functions or to use at different locations.

Control unit 36 may be used in conjunction with a host computer for a variety of input/output functions. For example, the control unit may be used to input commands, such as signals to start and stop the instrument. Similarly, the control unit may be used to display output information, such as instrument status, instrument diagnostics, measurement results, and other information generated by the analyzer in different assay modes. The control unit is especially useful for automated operations that require manual user intervention.

Figure 2:
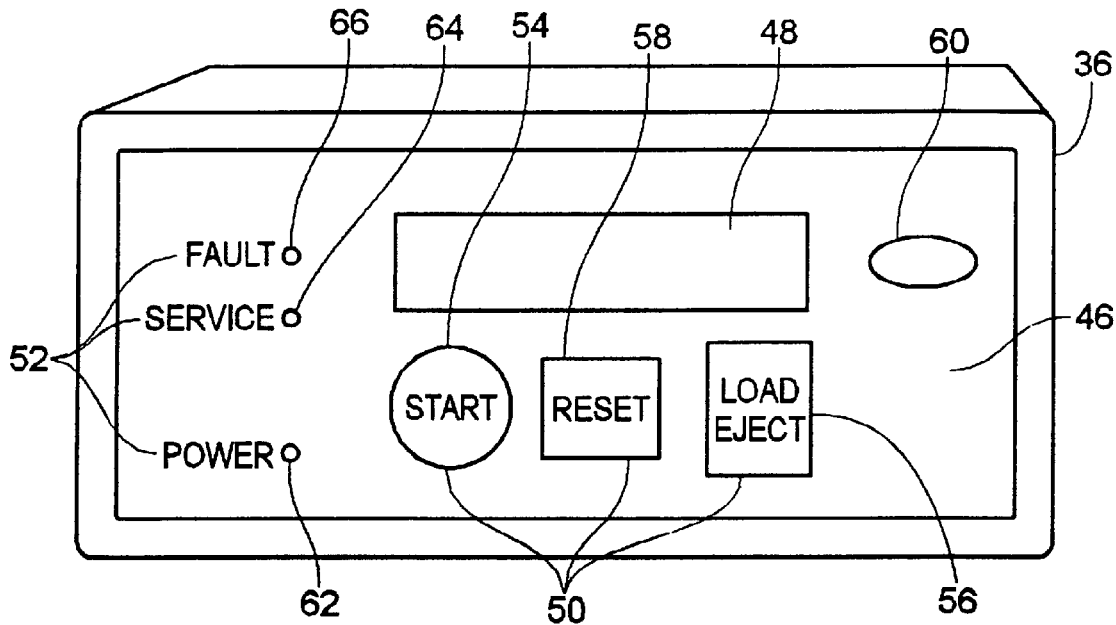
FIG. 2 is a front view of the face of a control unit.

FIG. 2 shows an enlarged isolated view of control unit 36 of analyzer 20. Control unit 36 is a separate unit that statically or swivelably affixes to the analyzer at any one of a plurality of docking locations. Control unit 36 is substantially L-shaped, with substantially perpendicular inner surfaces 44a,b that mate with adjacent substantially perpendicular walls of the analyzer including top wall 24 and one of side walls 26a–d, although other shapes are possible. In its preferred orientation, control unit 36 is mounted so that front face 46 is substantially parallel with one of side walls 26a–d of analyzer 20.

Control unit 36 includes various data input and output components. Front face 46 includes a gas-plasma display 48, keypad 50, and indicator lights 52. Control unit 36 also may include additional and/or alternative components, and their relative organization may deviate from that shown in the drawings and discussed below. Gas-plasma display 48 is located in the upper center of front face 46 and is used to provide messages regarding instrument status. Additional displays and/or alternative display formats, such as light-emitting diodes (LEDs) and liquid crystal displays (LCDs), also may be used.

Keypad 50 is located below and to the right of gas-plasma display 48 and includes four keys. A "start" key 54 initiates the sample-reading process. A "load/eject" key 56 loads or ejects a sample container, such as a microplate, depending upon the current status of the instrument. A "reset" key 58 reinitializes the instrument, sending motors to their home positions and turning off the audible alarm. A "status" key 60 alters the state of a continuous light source or reverses the stack. Additional keypads and additional and/or alternative keys also may be employed. Alternative methods of data entry, such as a computer mouse or touch screen, also may be employed.

Indicator lights 52 are located to the left of the display and keypad. A "power" light 62 indicates that power is being supplied to the instrument. A "service" light 64 indicates that a service procedure is needed, such as changing a light source. A "fault" light 66 indicates that a critical fault has occurred, which is a fault that requires intervention by an operator. Additional and/or alternative indicator lights also may be provided.

Control unit 36 also may include audio signals. For example, an audible alarm within the interior of control unit 36 may sound in the event of a critical fault. Alternative audio signals, such as prerecorded or synthesized voice messages, also may be used.

Control unit 36 may be moved between at least two control interface docking locations 68a,b on the instrument. A first docking location 68a is located near an upper edge of sample input side 26b of housing 22. This configuration is especially suitable for manual operation, because control unit 36 and transporter port 32 are positioned on the same side of analyzer 20. A second docking location 68b is located near an upper edge of back side 26d of housing 22. This configuration is especially suitable for robotic operation, because control unit 36 and transporter port 32 are positioned on opposite side of analyzer 20, facilitating robotic access to transporter port 32. Such flexible positioning permits commands to be entered and status information, diagnostic information, measurements, and other information to be read from multiple positions. Flexible positioning is especially convenient when one or more sides of the analyzer are blocked due to analyzer placement or nearby peripherals. Alternatively, it permits two or more control units to be connected at once, increasing convenience and flexibility.

Figure 3:
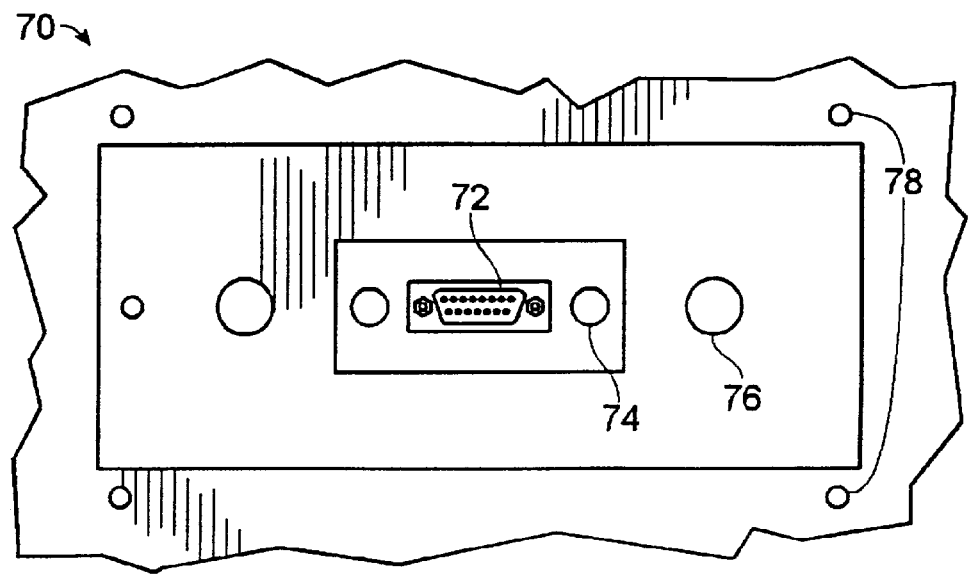
FIG. 3 is a partially schematic top view of a control interface docking location for a control unit.

FIG. 3 shows a control interface docking location 70. Control unit 36 includes an electronic connector prong, which can be mated with an electronic connector port 72 at docking location 70. Electronic connector port 72 is connected to a host computer, allowing the computer to communicate with the control unit, so that a user can control the analyzer by inputting information through the control unit. Electronic connector port 72 preferably includes an RS-232 serial port, and preferably is connected to the host computer through an RS-232 cable. Control unit 36 also includes other mating structure, including substantially cylindrical prongs that match with receptors 74 and latches 76, and indentations that match with dimples 78, at docking location 70. Positioning docking location 70 at sites 68a,b on top wall 24 of housing 22 reduces the stress on the mating structure when the control unit is mounted; however, docking location 70 also can be positioned at other sites on or off housing 22.

Accordingly, while the invention has been disclosed in its preferred form, the specific embodiment thereof as disclosed and illustrated herein is not to be considered in a limiting sense, because numerous variations are possible and no single feature, function, or property of the preferred embodiment is essential. The invention is to be defined only by the scope of the issued claims.

We claim:

1. A device for controlling an analyzer, the device comprising:

a plurality of control interface docking locations disposed on an analyzer housing; and a control unit that can be removably mounted at any one of the docking locations on the analyzer housing, so that a user can control the analyzer by inputting information through the control unit;

wherein the control unit can be moved from one docking location to another to provide convenience in different modes of operation.

2. The device of claim 1, wherein the control unit includes data input and output components.

3. The device of claim 1, wherein the control unit is L-shaped and configured to mount on a top edge of the housing.

4. The device of claim 1, wherein the control unit has a horizontal panel portion for resting on a top portion of the housing, and a vertical panel portion for resting against a side portion of the housing adjacent the top portion.

5. The device of claim 4, wherein an inner side of one of the panels has mating structure that compliments other mating structure provided at each of the docking locations.

6. The device of claim 1, wherein the housing has a sample input side, a first docking location being located near an upper edge of the sample input side.

7. The device of claim 6, wherein the housing has a back side opposite the sample input side, a second docking location being located near an upper edge of the back side of the housing.

8. The device of 1, wherein the control unit has a front face containing a display screen for indicating instrument status data.

9. The device of claim 8, wherein the front face of the control unit contains at least one data input button for carrying-out one or more of the following command functions: start, reset, load, and eject.

10. The device of claim 8, wherein the front face of the control unit contains at least one light indicator for indicating one or more of the following data output functions: power, fault, and service required.

11. The device of claim 1, wherein a first control interface docking location is positioned to provide convenience for manual operation of the analyzer, and wherein a second control interface docking location is positioned to provide convenience for robotic operation of the analyzer.

12. The device of claim 1, further comprising a second control unit, wherein a user can control the analyzer by inputting information through either control unit.

13. A device for controlling an analyzer, the device comprising:
   a first control interface docking location on or near an upper edge of a first side of a housing containing the analyzer, wherein the first side also includes a sample input port; and
   a control unit that can be operatively mounted at the first control interface docking location;
   wherein the control unit can be operatively relocated at a second control interface docking location remote from the first side of the housing.

14. The device of claim 13, wherein the second control interface docking location is located on or near a second side of the housing.

15. The device of claim 13, wherein the second control interface docking location is spaced apart from the housing.

16. The device of claim 11, further comprising a second control unit, wherein a user can control the analyzer by inputting information through either control unit.

17. The device of claim 13, wherein the first control interface docking location is positioned to provide convenience for manual operation of the analyzer, and wherein the second control interface docking location is positioned to provide convenience for robotic operation of the analyzer.

18. A method of controlling an analyzer capable of being used in a manual mode or a robotic mode, the method comprising:
   providing a control unit that can be mounted at a first or second docking location, wherein the docking locations are disposed on a housing containing the analyzer;
   mounting the control unit in the first docking location when the analyzer is to be used in the manual mode; and
   mounting the control unit in the second docking location when the analyzer is to be used in the robotic mode.

19. An analyzer for performing analysis on a sample, the analyzer comprising:
   a mechanism for performing analysis on the sample;
   a housing configured to contain the mechanism, wherein a plurality of control interface docking locations are disposed on the housing; and
   a control unit that can be removably mounted at any one of the docking locations.

20. The device of claim 19, wherein the control unit can be moved from one docking location to another to provide convenience in different modes of operation.

21. The device of claim 20, wherein a first control interface docking location is positioned to provide convenience for manual operation of the analyzer, and wherein a second control interface docking location is positioned to provide convenience for robotic operation of the analyzer.

22. The device of claim 19, wherein the analyzer is a light detection device.

* * * * *

UNITED STATES PATENT AND TRADEMARK OFFICE
CERTIFICATE OF CORRECTION

PATENT NO.   : 6,025,985
DATED        : February 15, 2000
INVENTOR(S)  : Lev J. Leytes et al.

It is certified that error appears in the above-identified patent and that said Letters Patent is hereby corrected as shown below:

Column 6,
Line 3, delete "11", and insert -- 13 -- therefor.

Signed and Sealed this

Twenty-fifth Day of March, 2003

JAMES E. ROGAN
*Director of the United States Patent and Trademark Office*